United States Patent
Bono et al.

(10) Patent No.: US 11,857,351 B2
(45) Date of Patent: Jan. 2, 2024

(54) ROBOTIC SURGICAL SYSTEM AND METHOD

(71) Applicant: GLOBUS MEDICAL, INC., Audubon, PA (US)

(72) Inventors: Peter L. Bono, Bingham Farms, MI (US); James D. Lark, West Bloomfield, MI (US); John S. Scales, Ann Arbor, MI (US); Thomas J. Lord, South Milwaukee, WI (US)

(73) Assignee: GLOBUS MEDICAL, INC., Audubon, PA (US)

( * ) Notice: Subject to any disclaimer, the term of this patent is extended or adjusted under 35 U.S.C. 154(b) by 429 days.

(21) Appl. No.: 16/676,092

(22) Filed: Nov. 6, 2019

(65) Prior Publication Data
US 2020/0138537 A1     May 7, 2020

Related U.S. Application Data

(60) Provisional application No. 62/756,377, filed on Nov. 6, 2018.

(51) Int. Cl.
| | |
|---|---|
| *A61B 50/22* | (2016.01) |
| *A61B 34/35* | (2016.01) |
| *A61B 34/30* | (2016.01) |
| *A61B 17/00* | (2006.01) |

(52) U.S. Cl.
CPC .............. *A61B 50/22* (2016.02); *A61B 34/30* (2016.02); *A61B 34/35* (2016.02); *A61B 2017/00464* (2013.01)

(58) Field of Classification Search
CPC ...... A61B 17/7082; A61B 2017/00464; A61B 2090/031; A61B 34/30; A61B 34/35; A61B 50/22; A61B 90/50; B25J 15/0416; B25J 15/0491
See application file for complete search history.

(56) References Cited

U.S. PATENT DOCUMENTS

| | | |
|---|---|---|
| 1,154,159 A | 9/1915 | Ashworth |
| 2,557,429 A | 6/1951 | Hawley |
| 2,831,295 A | 4/1958 | Weiss |
| 3,091,060 A | 5/1963 | Giegerich et al. |

(Continued)

FOREIGN PATENT DOCUMENTS

| | | |
|---|---|---|
| AR | 42807 | 7/2005 |
| AT | 370608 | 4/1983 |

(Continued)

OTHER PUBLICATIONS

Norton, D., "Tool stand common parts for QC-5 thru 21", Retrieved from Internet Apr. 2020: https://www.ati-ia.com/App_Content/Documents/9230-20-2012.auto.pdf, pp. 1-1, XP055684023, (Oct. 21, 2014).

(Continued)

*Primary Examiner* — Scott Luan

(57) ABSTRACT

A robotic surgical system is provided that includes a robot connected to a computer system to help effect control of the robot. A tool is removably mounted to a distal end of a robot arm. The tool is adapted to selectively grip, move and drive an effector and a coupled fastener. The fastener is used in orthopedic surgery, and the effector is uncoupled from the fastener after it is inserted in a patient.

14 Claims, 5 Drawing Sheets

(56) References Cited

U.S. PATENT DOCUMENTS

| | | |
|---|---|---|
| 3,554,197 A | 1/1971 | Dobbie |
| 3,577,579 A | 5/1971 | Duve |
| 3,876,255 A | 4/1975 | Ilon |
| 4,007,528 A | 2/1977 | Shea et al. |
| 4,008,720 A | 2/1977 | Brinckmann et al. |
| 4,081,704 A | 3/1978 | Vassos et al. |
| RE29,736 E | 8/1978 | Shea et al. |
| D248,967 S | 8/1978 | Shea et al. |
| 4,111,208 A | 9/1978 | Leuenberger |
| 4,596,243 A | 6/1986 | Bray |
| 4,620,539 A | 11/1986 | Andrews et al. |
| 4,828,052 A | 5/1989 | Duran et al. |
| 4,932,935 A | 6/1990 | Swartz |
| 5,092,875 A | 3/1992 | McLees |
| 5,522,829 A | 6/1996 | Michalos |
| 5,733,119 A | 3/1998 | Carr |
| 5,843,110 A | 12/1998 | Dross et al. |
| 6,021,538 A | 2/2000 | Kressner et al. |
| 6,110,174 A | 8/2000 | Nichter |
| 6,236,875 B1 | 5/2001 | Bucholz et al. |
| 6,490,467 B1 | 12/2002 | Bucholz et al. |
| 6,546,279 B1 | 4/2003 | Bova et al. |
| 6,547,340 B2 | 4/2003 | Harris |
| 6,635,067 B2 | 10/2003 | Norman |
| 6,676,669 B2 | 1/2004 | Charles et al. |
| 6,689,087 B2 | 2/2004 | Pal et al. |
| 6,716,215 B1 | 4/2004 | David et al. |
| 6,721,986 B2 | 4/2004 | Zhuan |
| 6,966,912 B2 | 11/2005 | Michelson |
| 7,160,304 B2 | 1/2007 | Michelson |
| 7,194,120 B2 | 3/2007 | Wicker et al. |
| 7,346,417 B2 | 3/2008 | Luth et al. |
| 7,922,720 B2 | 4/2011 | May et al. |
| 7,980,335 B2 | 7/2011 | Potter |
| 8,029,523 B2 | 10/2011 | Wallis et al. |
| 8,038,630 B2 | 10/2011 | Pal et al. |
| 8,170,717 B2 | 5/2012 | Sutherland et al. |
| 8,219,178 B2 | 7/2012 | Smith et al. |
| 8,465,491 B2 | 6/2013 | Yedlicka et al. |
| 8,491,603 B2 | 7/2013 | Yeung et al. |
| 8,657,821 B2 | 2/2014 | Palermo |
| 8,728,085 B2 | 5/2014 | Marsh et al. |
| 8,828,001 B2 | 9/2014 | Stearns et al. |
| 8,894,654 B2 * | 11/2014 | Anderson ............... A61B 17/17 606/80 |
| 8,943,634 B2 | 2/2015 | Sokol et al. |
| 2003/0060927 A1 | 3/2003 | Gerbi et al. |
| 2004/0050603 A1 | 3/2004 | Jaeger |
| 2004/0147934 A1 | 7/2004 | Kiester |
| 2004/0199072 A1 | 10/2004 | Sprouse et al. |
| 2005/0027397 A1 | 2/2005 | Niemeyer |
| 2005/0043718 A1 | 2/2005 | Madhani et al. |
| 2005/0171557 A1 | 8/2005 | Shoham |
| 2005/0283175 A1 | 12/2005 | Tanner |
| 2006/0229624 A1 | 10/2006 | May et al. |
| 2006/0235305 A1 | 10/2006 | Cotter et al. |
| 2006/0235306 A1 | 10/2006 | Cotter et al. |
| 2007/0021738 A1 | 1/2007 | Hasser et al. |
| 2007/0276423 A1 | 11/2007 | Green |
| 2007/0282344 A1 | 12/2007 | Yedlicka et al. |
| 2007/0282345 A1 | 12/2007 | Yedlicka et al. |
| 2008/0027449 A1 | 1/2008 | Gundlapalli et al. |
| 2008/0061784 A1 | 3/2008 | Pal et al. |
| 2008/0108010 A1 | 5/2008 | Wang |
| 2008/0108991 A1 | 5/2008 | von Jako |
| 2008/0213889 A1 | 9/2008 | Olgac |
| 2009/0222149 A1 | 9/2009 | Murray et al. |
| 2010/0145343 A1 | 6/2010 | Johnson et al. |
| 2010/0165793 A1 | 7/2010 | Haug |
| 2010/0198230 A1 | 8/2010 | Shoham |
| 2010/0249506 A1 | 9/2010 | Prisco |
| 2010/0249786 A1 | 9/2010 | Schmieding et al. |
| 2011/0015635 A1 | 1/2011 | Aryan |
| 2011/0015649 A1 | 1/2011 | Anvari et al. |
| 2011/0118708 A1 | 5/2011 | Burbank et al. |
| 2011/0118709 A1 | 5/2011 | Burbank |
| 2011/0118778 A1 | 5/2011 | Burbank |
| 2011/0196404 A1 | 8/2011 | Dietz et al. |
| 2011/0230886 A1 | 9/2011 | Gustilo et al. |
| 2011/0295270 A1 | 12/2011 | Giordano et al. |
| 2011/0306873 A1 | 12/2011 | Shenai et al. |
| 2011/0313428 A1 | 12/2011 | Mohr et al. |
| 2011/0319941 A1 | 12/2011 | Bar et al. |
| 2012/0059392 A1 | 3/2012 | Dolaiti |
| 2012/0173021 A1 | 7/2012 | Tsusaka |
| 2012/0186372 A1 | 7/2012 | Smith et al. |
| 2012/0211546 A1 | 8/2012 | Shelton, IV |
| 2012/0220831 A1 | 8/2012 | Cooper et al. |
| 2012/0266442 A1 | 10/2012 | Rogers et al. |
| 2013/0096540 A1 | 4/2013 | Cooper et al. |
| 2013/0123799 A1 | 5/2013 | Smith et al. |
| 2013/0178856 A1 | 7/2013 | Ye et al. |
| 2013/0206441 A1 | 8/2013 | Roser et al. |
| 2013/0244820 A1 | 9/2013 | Solomon et al. |
| 2013/0245629 A1 | 9/2013 | Xie |
| 2013/0296886 A1 | 11/2013 | Green et al. |
| 2013/0304069 A1 | 11/2013 | Bono et al. |
| 2013/0345718 A1 | 12/2013 | Crawford et al. |
| 2014/0051922 A1 | 2/2014 | Guthart et al. |
| 2014/0067121 A1 | 3/2014 | Brooks et al. |
| 2014/0100574 A1 | 4/2014 | Bono et al. |
| 2014/0194894 A1 | 7/2014 | Dachs, II et al. |
| 2014/0222003 A1 | 8/2014 | Herndon et al. |
| 2014/0276001 A1 | 9/2014 | Ungi et al. |
| 2014/0350391 A1 | 11/2014 | Prisco et al. |
| 2014/0350571 A1 | 11/2014 | Maillet et al. |
| 2015/0119916 A1 | 4/2015 | Dietz et al. |
| 2015/0133960 A1 * | 5/2015 | Lohmeier ............... A61B 90/40 606/130 |
| 2015/0355805 A1 | 12/2015 | Chandler et al. |
| 2016/0151120 A1 | 6/2016 | Kostrzewski et al. |
| 2017/0065248 A1 | 3/2017 | Ungi et al. |
| 2018/0168757 A1 * | 6/2018 | Bono ..................... A61B 34/30 |
| 2018/0200063 A1 | 7/2018 | Kahmer et al. |
| 2018/0214221 A1 * | 8/2018 | Crawford ............. B25J 15/0441 |
| 2018/0250142 A1 | 9/2018 | Zappacosta et al. |
| 2018/0289496 A1 | 10/2018 | Zappacosta et al. |
| 2018/0289501 A1 | 10/2018 | Seifert et al. |
| 2018/0289502 A1 | 10/2018 | Zappacosta et al. |
| 2018/0290154 A1 | 10/2018 | Baxter |

FOREIGN PATENT DOCUMENTS

| | | |
|---|---|---|
| AU | 2011215901 | 1/2003 |
| AU | 2003200831 | 8/2004 |
| BE | 861446 | 3/1978 |
| CA | 1112970 | 11/1981 |
| CA | 2513071 | 7/2004 |
| CA | 2788918 | 8/2011 |
| CH | 610753 | 5/1979 |
| CL | 252004 | 3/2005 |
| CN | 102781349 | 11/2012 |
| CN | 107951564 | 4/2018 |
| CN | 106361437 | 10/2018 |
| DE | 570977 | 2/1933 |
| DE | 2730227 | 12/1980 |
| DK | 197705709 | 6/1978 |
| EP | 148304 | 7/1985 |
| EP | 0261260 | 3/1988 |
| EP | 1571581 | 3/2005 |
| EP | 1041918 | 3/2006 |
| EP | 1581374 | 8/2006 |
| EP | 1690649 | 8/2006 |
| EP | 2533703 | 12/2012 |
| ES | 465719 | 12/1980 |
| FI | 773650 | 6/1978 |
| FR | 2374886 | 7/1978 |
| GB | 1550577 | 8/1979 |
| IT | 1081824 | 5/1985 |
| JP | 2006512954 | 4/2006 |
| JP | 4481173 | 6/2010 |
| JP | 2013519434 | 5/2013 |
| JP | 5380789 | 1/2014 |
| JP | S5613462 | 10/2014 |

(56) References Cited

FOREIGN PATENT DOCUMENTS

| | | |
|---|---|---|
| JP | 5826771 | 12/2015 |
| NL | 7713563 | 6/1978 |
| NO | 774411 | 6/1978 |
| WO | WO9107116 | 5/1991 |
| WO | WO9927839 | 6/1999 |
| WO | WO0215799 | 2/2002 |
| WO | WO2004062863 | 7/2004 |
| WO | WO2007008703 | 1/2007 |
| WO | WO2009151926 | 12/2009 |
| WO | WO2011100313 | 8/2011 |
| WO | WO20122166476 | 12/2012 |
| WO | WO2014150514 | 9/2014 |
| WO | WO2015006296 | 1/2015 |
| WO | WO2015166487 | 11/2015 |
| WO | WO2017163251 | 9/2017 |

OTHER PUBLICATIONS

Cutting Tool, Drill Bit, End Mill, Internet catalogue, http://lzqtool.com/include/search.aspx?keycode=c-grade&type=1&language=en, (Retrieved Feb. 7, 2018).

Tungsten Carbide Drills Mills & Burs, Internet catalogue, http://chinatungsten.com/picture-bank/tungsten-carbide-drills.html, (Retrieved Feb. 7, 2018).

News & Notes, British Dental Journal, vol. 191, No. 7, pp. 410-411 (Oct. 13, 2001).

MasterCut Tool Corp., Bur Series, US, (2010).

MasterCut Tool Corp., Bur Series, Metric, (2018).

\* cited by examiner

ROBOTIC SURGICAL SYSTEM AND METHOD

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/756,377, entitled "ROBOTIC SURGICAL SYSTEM AND METHOD", filed Nov. 6, 2018. The contents of the above referenced application is incorporated herein by reference in its entirety.

FIELD OF THE INVENTION

The present invention relates to surgical systems and methods, and more particularly, to a multi-axis robotic device having an end effector constructed to install screws in a patient's orthopedic structure, such as a spine component.

BACKGROUND OF THE INVENTION

The central nervous system is a vital part of the human physiology that coordinates human activity. It is primarily made up of the brain and the spinal cord. The spinal cord is made up of a bundle of nerve tissue, which originates in the brain and branches out to various parts of the body, acting as a conduit to communicate neuronal signals from the brain to the rest of the body, including motor control and sensations. Protecting the spinal cord is the spinal, or vertebral, column. Anatomically, the spinal column is made up of several regions including the cervical, thoracic, lumbar and sacral regions. The cervical spine is made up of seven vertebrae and functions to support the weight of the head. The thoracic spine is made up of twelve vertebrae and functions to protect the organs located within the chest. Five vertebrae make up the lumbar spine. The lumbar spine contains the largest vertebrae and functions as the main weight-bearing portion of the spine. Located at the base of the spine are the five fused vertebrae known as the sacrum. The coccyx sits at the base of the spinal column and consists of four fused vertebrae.

Each of the vertebrae associated with the various spinal cord regions are made up of a vertebral body, a posterior arch, and transverse processes. The vertebral body, often described as having a drum-like shape, is designed to bear weight and withstand compression or loading. In between the vertebral bodies is the intervertebral disc. The intervertebral disc is filled with a soft, gelatinous-like substance that helps cushion the spine against various movements and can be the source of various diseases. The posterior arch of the vertebrae is made up of the lamina, pedicles and facet joints. Transverse processes extend outwardly from the vertebrae and provide the means for muscle and ligament attachment, which aid in movement and stabilization of the vertebra.

While most people have fully functional spinal cords, it is not uncommon for individuals to suffer some type of spinal ailment, including spondylolisthesis, scoliosis, or spinal fractures. One of the more common disorders associated with the spinal cord is damage to the spinal discs. Damage to the discs results from physical injury, disease, genetic disposition, or as part of the natural aging process. Disc damage often results in intervertebral spacing not being maintained, causing pinching of exiting nerve roots between the discs, resulting in pain. For example, disc herniation is a condition in which the disc substance bulges from the disc space between the two vertebrae bodies. It is the bulging of the disc material that causes impingement on the nerves, manifesting in pain to the patient. For most patients, rest and administration of pain and anti-inflammatory medications alleviates the problem. However, in severe cases, cases which have developed into spinal instability or severe disc degeneration, the damaged disc material between the vertebral bodies is removed and replaced with spinal stabilization implants. Restoration to the normal height allows the pressure on the nerve roots to be relieved.

There are many different approaches taken to alleviate or reduce severe spinal disorder. One surgical procedure commonly used is a spinal fusion technique. Several surgical approaches have been developed over the years, and include the Posterior Lumbar Interbody Fusion (PLIF) procedure which utilizes a posterior approach to access the patient's vertebrae or disc space; the Transforaminal Lumbar Interbody Fusion (TLIF) procedure which utilizes a posterior and lateral approach to access the patient's vertebrae or disc space; and the Anterior Lumbar Interbody Fusion (ALIF) which utilizes an anterior approach to access the patient's vertebrae or disc space. Using any of these surgical procedures, the patient undergoes spinal fusion surgery in which two or more vertebrae are linked or fused together through the use of a bone spacing device and/or use of bone grafts. The resulting surgery eliminates any movement between the spinal sections that have been fused together.

In addition to the spinal implants or use of bone grafts, spinal fusion surgery often utilizes spinal instrumentation or surgical hardware, such as pedicle screws, plates, or spinal rods. Once the spinal spacers and/or bone grafts have been inserted, a surgeon places the pedicle screws into a portion of the spinal vertebrae and attaches either rods or plates to the screws as a means for stabilization while the bones fuse. Currently available systems for inserting the rods into pedicle screws can be difficult to use, particularly in light of the fact that surgeons installing these rods often work in narrow surgical fields. Moreover, since patients can vary with respect to their internal anatomy, resulting in varying curvatures of the spine, a surgeon may not always have a linear path, or may have to maneuver around anatomical structures in order to properly insert the surgical rods into the pedicle screw assemblies. In addition to needed surgical skill, difficulty in placing the rods correctly into the pedicle screws can result in unnecessary increases in the time it takes a surgeon to complete the surgical procedure. Prolonged surgery times increase the risk to the patient. More importantly, improperly aligning the rods and pedicle screw assemblies often results in post-surgery complications for the patient and requires corrective surgical procedures.

Robotic surgery, computer-assisted surgery, and robotically-assisted surgery are terms for technological developments that use robotic systems to aid in surgical procedures. Robotically-assisted surgery was developed to overcome the limitations of pre-existing minimally-invasive surgical procedures and to enhance the capabilities of surgeons performing open surgery.

In the case of robotically-assisted minimally-invasive surgery, instead of directly moving the instruments, the surgeon uses one of two methods to control the instruments; either a direct telemanipulator or through computer control. A telemanipulator is a remote manipulator that allows the surgeon to perform the normal movements associated with the surgery while the robotic arms carry out those movements using end-effectors and manipulators to perform the actual surgery on the patient. In computer-controlled systems, the surgeon uses a computer to control the robotic arms and its end-effectors, though these systems can also still use telemanipulators for their input. One advantage of using the computerized method is that the surgeon does not have to be present, but can be anywhere in the world, leading to the possibility for remote surgery. One drawback relates to the lack of tactile feedback to the surgeon. Another drawback relates to visualization of the surgical site. Because the surgeon may be remote or the surgery may be percutaneous, it is difficult for the surgeon to view the surgery as precisely as may be needed.

There exists, therefore, a need for a robotic system that can be used by a surgeon to easily and safely remove or modify bone, cartilage and disk material for orthopedic procedures, particularly, but not limited to the spine. The robotic surgical system should provide a tool change station that includes a variety of surgical tools and implants needed for completion of a particular operation. The tool change station should locate and hold the surgical tools and implants in a manner that allows the robot to drop a tool and pick up another tool or implant for use in the procedure. The tools and implants may be of various sizes and shapes of which the robot knows, and may include but should not be limited to profiles and dimensions for length, width, diameter, weight, center of gravity, and the like. Thus, when the tool is changed the robot can maneuver each tool with precision while avoiding obstacles and patient anatomy.

DESCRIPTION OF THE PRIOR ART

The art is replete with surgical robots. In general, a robot has multiple components that allow one or more axes of movement of a device mounted to a distal end of the robot for use in surgery. Numerous such devices are known in the art. They can include cutters, grinders, gripping devices, force applying devices and the like. Numerous surgical robots are available on the market, and include brands such as Kuka, Versius, Da Vinci and Mako. Robots are designed to grip and manipulate effectors to perform programmed functions. They are currently only designed to change effectors upon the removal of fasteners and the like which secure the effector to the robotic arm. A controlling computer knows the location of each effector and is operable to control operation of the attached effector through the robot arm.

The present invention provides an improvement in surgical robots and their operation, particularly for the ability to utilize a plurality of tools needed for completion of a surgical procedure, including the insertion of implants and threaded fasteners.

SUMMARY OF THE INVENTION

The present invention provides a surgical robot system having a plurality of tools, which can be interchanged as needed for the completion of a surgical procedure. The controlling computer stores the location, profile and dimensions of the tools so that, as the tools are utilized, the robot can position and maneuver them with the precision required to complete complex surgical operations. Implants may be additionally stored according to size and profile in a manner that allows the robot to pick a desired implant for insertion into a patient. The implant may be utilized by itself or, alternatively, a tool may be changed to be the end effector of the surgical robot, the tool used to grasp an implant, whereby the controller is suited to determine the length, diameter and profile of the implant and tool combination.

Accordingly, it is a primary objective of the present invention to provide a surgical robot that can be manipulated and controlled to pick and change a variety of surgical tools stored in a magazine.

It is a further objective of the present invention to provide a surgical robot that can retain the dimensions and/or profiles of various tools that are utilized when the particular tool is selected for use.

It is yet a further objective of the present invention to provide a tool magazine that positions a plurality of tools in a position suitable for the surgical robot to interchange the tools.

It is still yet another objective of the present invention to provide a tool change system that allows a first tool to be grasped and thereafter allow that first tool to grasp or couple to another tool or implant that works in conjunction with the first tool.

Yet another objective of the present invention is to provide a surgical tool that can be used to install more than one fastener in sequence and separate itself from a used effector, allowing a new effector and associated fastener to be coupled for use.

Still yet another objective of the present invention is to provide an implant coupled to a portion of an end effector in a magazine such that a tool can be changed to be a current end effector to couple with the portion of the end effector secured to the implant for insertion into a patient.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE INVENTION

Figure 1:
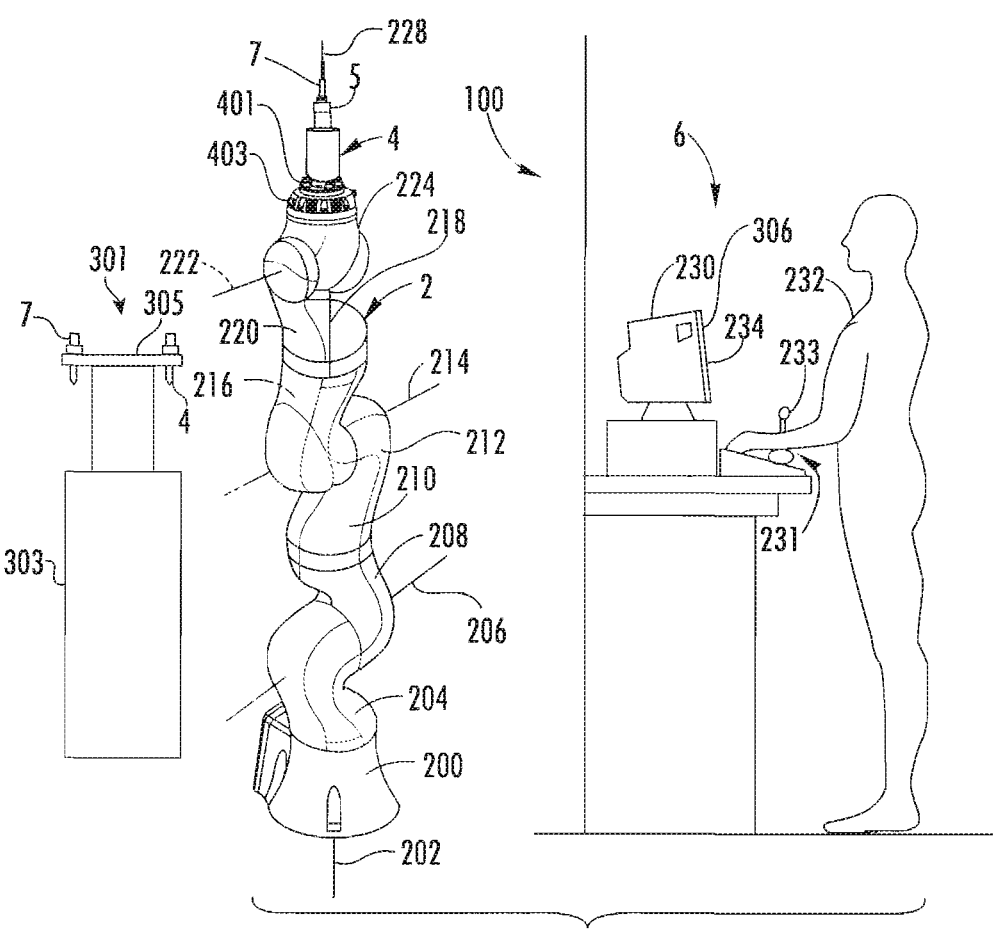
FIG. 1 illustrates one embodiment of the multi-axis robot along with an operator station.

Referring to FIG. 1, a robotic surgical system 100 is illustrated. The robotic surgical system 100 generally includes a multi-axis robot 2, a tool 4 with an effector attachment device 5 on a distal end thereof, and an operator station 6. Such a multi-axis robot 2 is disclosed in our Patent Application Nos. 62/616,673, 62/681,462, 62/423,651, 62/616,700, and Ser. No. 15/816,861 to Peter L. Bono. These applications disclose robotic surgical systems usable with the present system. The entireties of these disclosures are incorporated herein by reference. The tool 4 couples to the robot 2 via a tool changer 9 as described below. The tool 4 couples to and powers an effector in the form of a fastener driver 7 for rotation, as more fully described below. The multi-axis robot 2 includes a plurality of axes about which the tool 4 can be precisely maneuvered and oriented for surgical procedures. In a preferred, but non-limiting, illustrated embodiment, the multi-axis robot 2 includes seven axes of movement. The axes of movement include the base axis 202, or first axis, which is generally centered within the base 200 and about which the first arm 204 rotates. The second axis 206 is substantially perpendicular to the first axis 202 and the axis about which the second arm 208 rotates. The second arm 208 includes the third axis 210 about which the third arm 212 rotates. The third arm 212 includes the fourth axis of rotation 214, which is oriented substantially perpendicular with respect to the first axis 202 and substantially parallel to the second axis 206. The fourth arm 216 rotates about the fourth axis 214. The fourth arm 216 includes the fifth axis 218 about which the fifth arm 220 rotates. The fifth arm 220 includes the sixth axis 222, which includes the most available rotation about the sixth axis 222 for the wrist 224 of the robot. The wrist 224 carries the tool 4 and effector attachment device 5, and has a seventh axis of rotation 228 for the driver 7 of the tool 4. The driver 7 is an effector that is operable to drive a threaded fastener, such as a screw 8 or the like, for example, a bone screw or pedicle screw. The wrist 224 is at the distal end of the fifth arm 220. It should be noted that each axis of rotation provides an additional freedom of movement for manipulation and orientation of the tool 4 and hence driver 7. It should also be noted that while the multi-axis robot 2 is only illustrated with the tool 4, the preferred embodiment is capable of changing the effector to a variety of tools that are used to complete a particular surgery. Drives, not shown, are utilized to move the arms into their desired positions and orientations. The drives may be electric, hydraulic or pneumatic and combinations thereof without departing from the scope of the invention. Rotational position can be signaled to a computer 230, as with an encoder (not shown), or the like, associated with each arm 204, 208, 212, 216, 220, and other components having an axis of rotation. In the preferred embodiment, the drives are in electrical communication with the computer 230, and may further be combined with a telemanipulator, or pendant (not shown). The computer 230 is programmed to control movement and operation of the robot(s) 2 through a controller portion 231, and can utilize a software package such as that disclosed in U.S. Patent Application No. 62/616,700 to the present inventor. Alternatively, other software programming may be provided without departing from the scope of the invention. The computer 230 can have a primary storage device (commonly referred to as memory) and/or a secondary storage device that can be used to store digital information such as images. Primary and secondary storage are herein referred to as storage collectively, and can include one or both primary and secondary storage. The system 100 may further include sensors positioned along various places on the multi-axis robot 2, which provide tactile feedback to the operator or surgeon 232. The computer 230 is electrically connected or coupled to the multi-axis robot 2 in a manner that allows for operation of the multi-axis robot 2, ranging from positions adjacent the robot to thousands of miles away. The computer 230 is preferably capable of accepting, retaining and executing programmed movements of the multi-axis robot 2 in a precise manner. In this manner, skilled surgeons can provide surgical care in areas, such as battlefields, while the surgeon is safe from harm's way. The controller 231 can include a movement control input device 233, such as a joy stick, keyboard, mouse or electronic screen 306 that can be touch activated. The screen 306 can be part of the monitor 234. Tool change and selection commands can be input using the screen 306.

Figure 4:
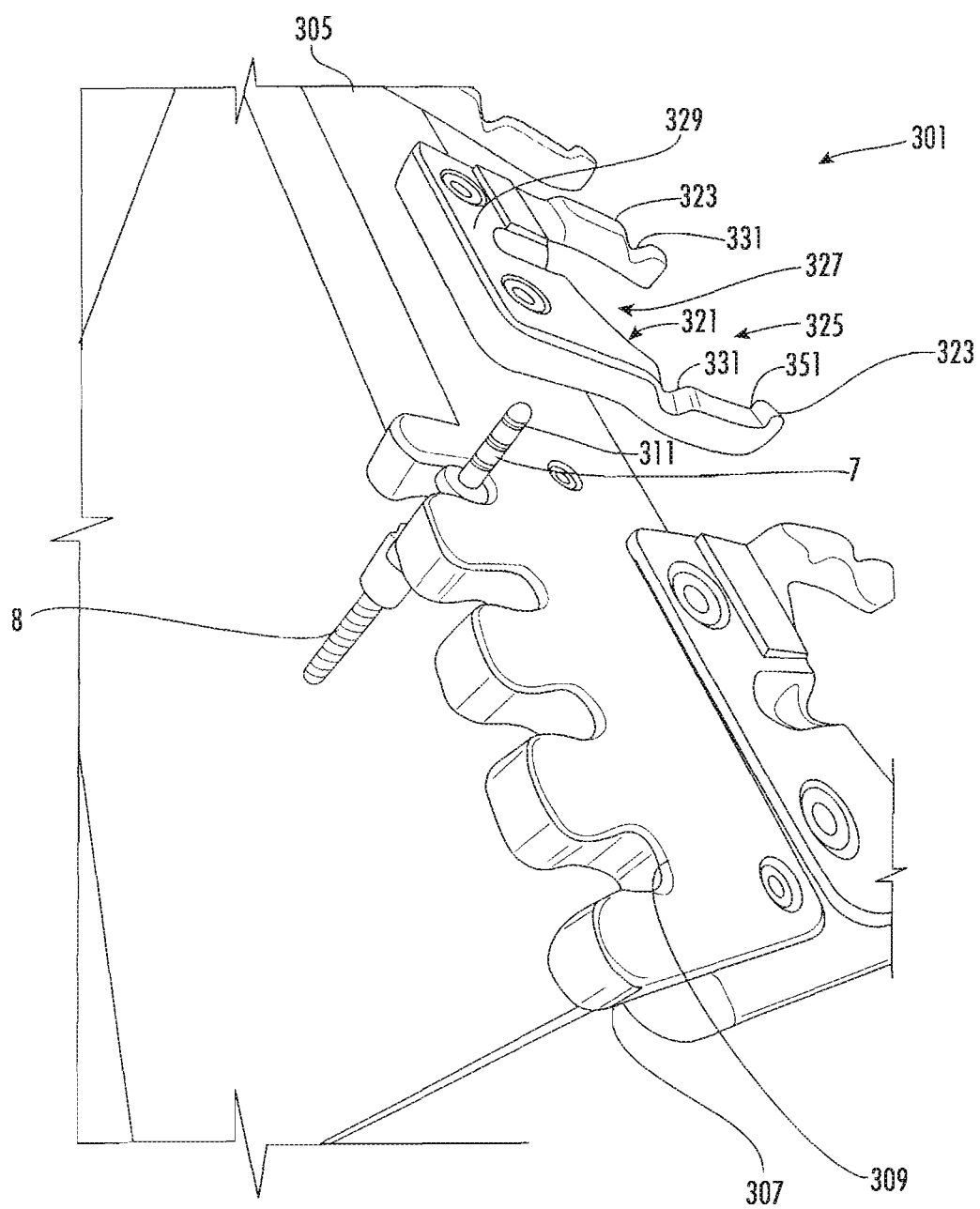
FIG. 4 is an isometric view of a magazine adapted to hold both tools and implants.
Figure 5:
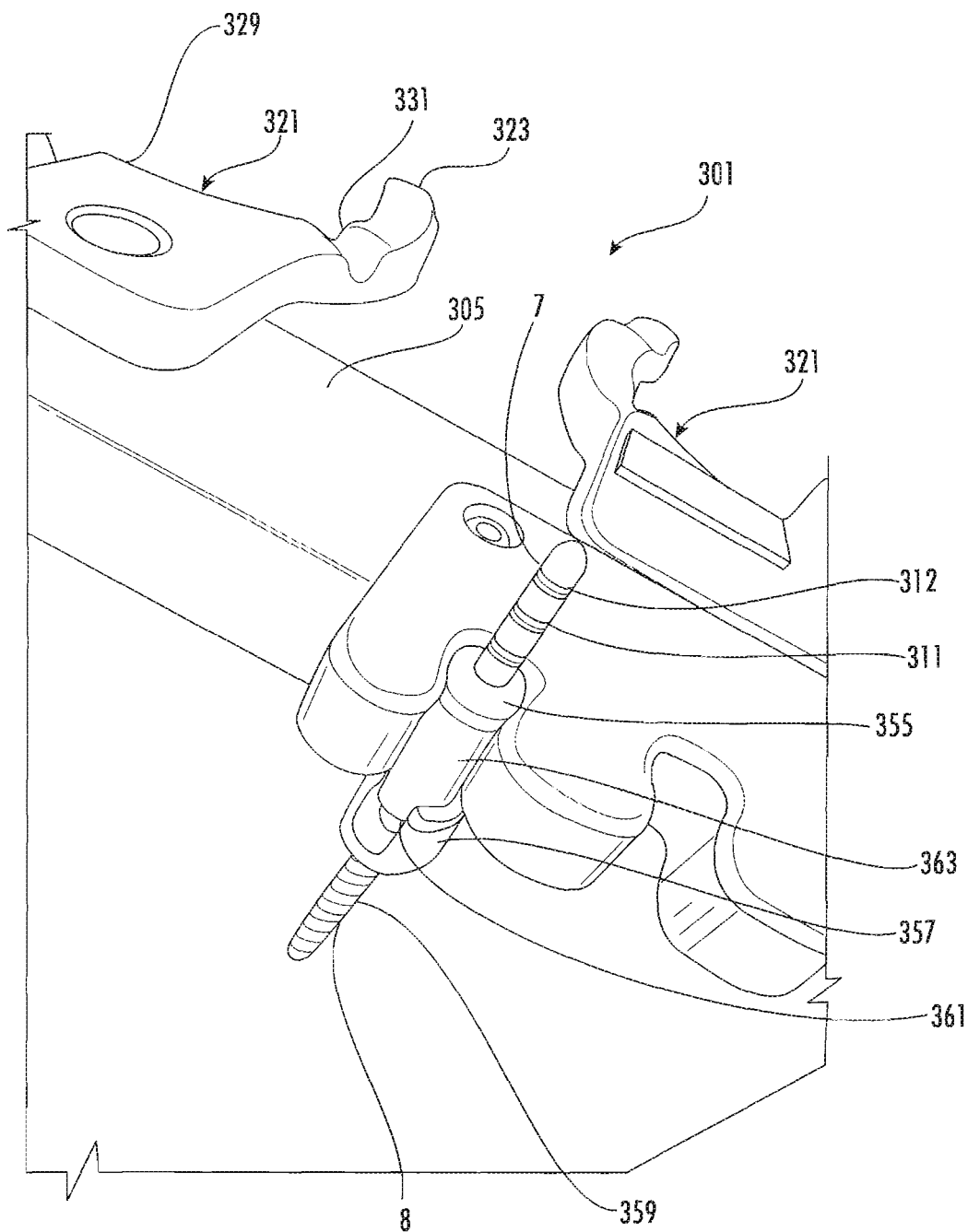
FIG. 5 is an enlarged isometric view of a portion of the magazine seen in FIG. 4.

As seen in FIG. 1, the robotic surgical system 100 includes a magazine 301 for holding of one or more tools 4 and one or more effectors, such as a secondary tool like the fastener driver 7, in positions for pickup and replacement by the robot 2. The tool 4 is mounted to the robot 2 using a tool changer, which is designated generally as 9. Such tool changers are known in the art, such as those made by ATI as models MC-16R, QC-11, and QC-21. As seen in FIGS. 1, 4 and 5, the magazine 301 includes a stand 303 positioned adjacent the robot 2 and a platform 305 that has one or more cradles mounted thereon. The cradles may include V-notches, clamps or the like that allow the tool 4 to be positioned repeatedly in a similar position to be picked up or dropped off by the robot. At least one effector cradle 307 is mounted on the platform 305 and is adapted to hold one or more effectors 7 (fastener driver), and preferably a fastener 8 coupled to each effector. As seen, the cradle 307 has a plurality of spaced apart open-end slots 309, each adapted to receive therein and hold in position a respective effector 7. In a preferred embodiment, an effector 7 has a shank 311 which projects generally vertically when stored in a cradle 307. However, it is to be understood that a magazine could be provided where the shanks 311 project in different directions than generally vertically. In the case of a generally vertical shank 311, removal of the effector 7 (driver) is effected by moving the effector 7 generally horizontally (laterally) out of a respective slot 309. In a preferred embodiment, a shank 311 has one or more circumferentially extending grooves 312 recessed in an outer surface for a purpose later described.

The magazine 301 also includes at least one cradle 321 configured for releasably holding one or more tools 4 in a manner and position to be extracted from the cradle for use and reinserted for storage. As shown, there are a plurality of cradles 321 that are substantially identical in shape, size and construction. A cradle 321 has a pair of spaced apart arms 323 with an open end space 325 between distal ends thereof. A through opening 327 is also provided between a pair of arms 323 and is in communication with the open space 325. This configuration allows a tool 4 to be removed or inserted by vertical and/or horizontal movement of the tool 4. As shown, the arms 323 of a cradle 321 are connected by a bight 329. Means is provided to releasably retain a tool 4 mounted in a respective cradle 321 while retaining the tool 4 in a known position so that the robot 2 can reliably locate the tool 4 for pickup for use and reinsertion after use for storage. As shown, upwardly facing surfaces of each of the arms 323 are provided with a plurality of upwardly opening V-shaped notches 331. The use of at least three notches 331 will define a plane so that the orientation and position of the tool 4 while mounted in the cradle 321 is known to the robot system 100 to facilitate coupling and decoupling of the tool 4 to the robot 2 via the tool changer 9. It should be noted that while V-shaped notches are illustrated, other shapes suitable for repeatably locating the tools can be utilized without departing from the scope of the invention.

A suitable effector is shown in FIG. 5. The effector 7 is in the form of a fastener driver that has a coupling shank 311 adapted for being releasably secured to the tool 4 with the attachment device 5 that is shown as including a chuck 351 (FIG. 3) associated with the tool 4 at its distal end 353. A positioning flange 355 extends laterally outwardly of the shank 311 for helping retain the driver 7 releasably mounted in its cradle 307 and limit its longitudinal movement into the chuck 351. In the illustrated embodiment, the fastener 8 is shown as a pedicle screw that has a tulip 357, as is known in the art. The tulip 357 is mounted to the screw portion 359 of the fastener 8. The tulip 357 has an internally threaded portion that threadably engages an externally threaded portion 361 of a terminal end portion 363 of the effector 7. The thread handedness of the threaded portion 361 is the same as the thread handedness of the screw portion 359, e.g., right handed. After the fastener 8 is installed, the tool 4 can effect reverse rotation, backing the threaded portion 361 out of the threaded portion of the tulip 357. It is to be noted here that the terminal end portion 363 can be constructed to break if a predetermined tightening torque is exceeded by the tool 4. If this occurs, the surgeon can then manually extract the remaining threaded portion 361 from the tulip 357.

Figure 2:
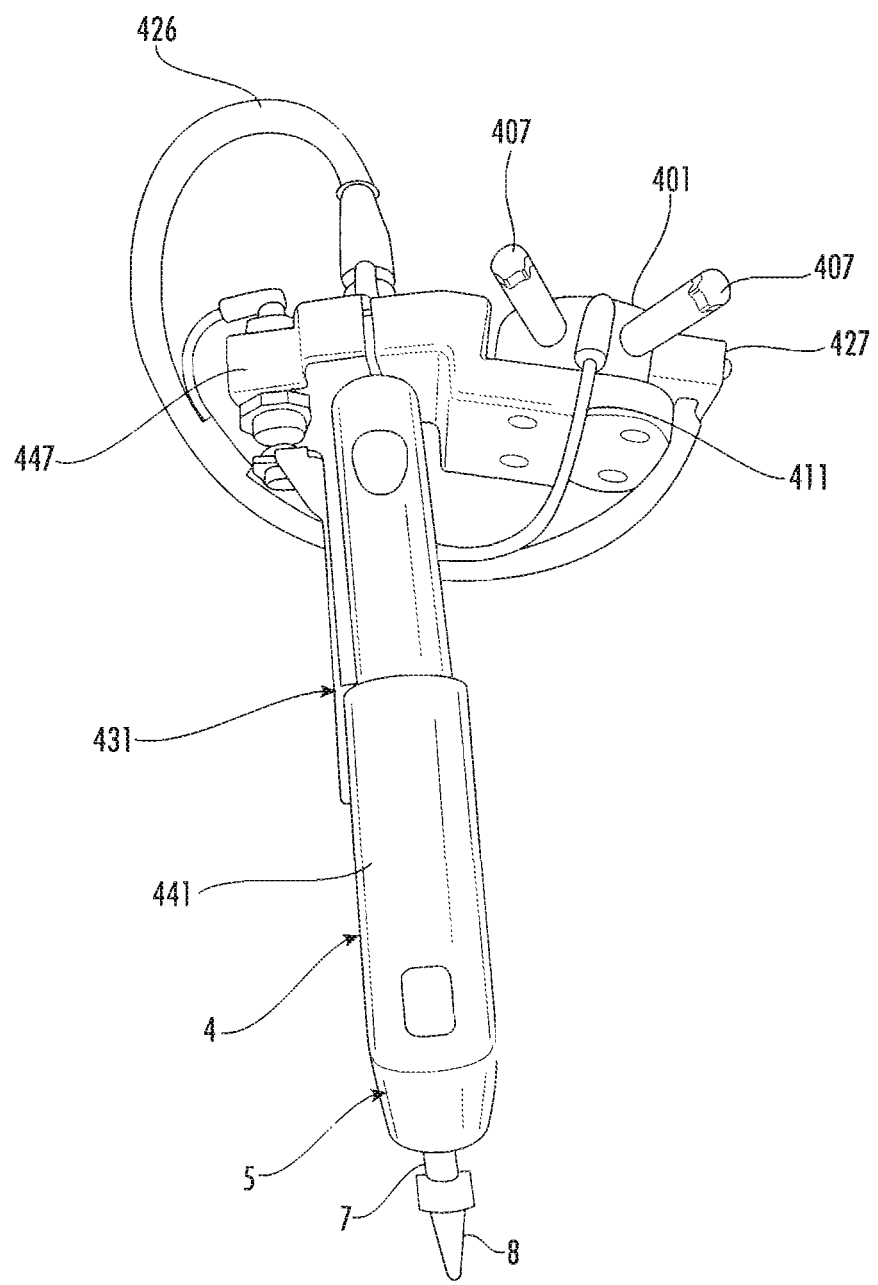
FIG. 2 is an isometric view of a surgical tool used as an end effector and suitable for coupling with a portion of an end effector for releasably retaining a surgical implant.
Figure 3:
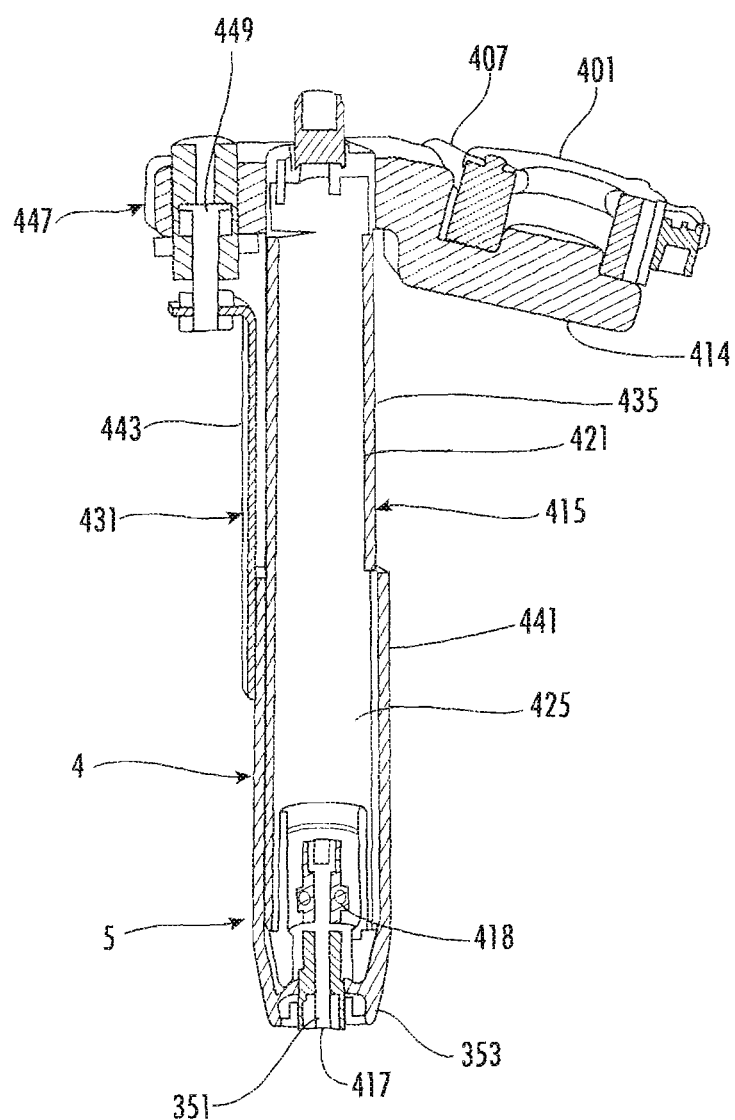
FIG. 3 is a sectional view of the tool shown in FIG. 2, illustrating a portion of the tool changer and the operable assembly for grasping a portion of the end effector and an implant.

The tool 4 is best seen in FIGS. 2, 3. The tool 4 includes a first coupling component 401. The coupling component 401 is configured to be releasably gripped by a second coupling component 403 that is mounted to the distal end wrist 224. The coupling components 401, 403 combine to form the tool changer 9, which is well known in the art, and allow for releasable mounting of tools and effectors to robot(s) 2. As shown, the coupling component 401 includes a plurality of outwardly projecting arms 407 that are each sized and shaped to be received in a respective notch 331 for releasably mounting of the tool 4 to a respective cradle 321. The coupling component 401 can be configured for supplying a compressed fluid, such as air from a source (not shown) of compressed fluid, through the robot 2 to a flow conduit 411 for a purpose later described. The coupling component 401 is mounted to a connecting arm 414, which in turn connects the coupling component 401 to a tool head 415. The chuck 351 is mounted in the tool head 415 at its distal end. The chuck 351 is constructed to releasably retain the shank 311 of the effector 7 within a socket portion 417 of the chuck 351. The chuck 351 can be provided with a ball detent arrangement 418, such as those found in air hose chucks, that cooperate with the grooves 312 to releasably retain a shank 311 in the chuck 351. A powered rotary driver 421, such as an electric motor or air motor, is mounted in the tool head 415, and is coupled to the chuck 351 to effect its driving of the effector 7 upon command from a control component of the surgical system 100, such as the operator station 6, which in turn can be controlled by the appropriate medical personnel or programming as described above. The rotary driver 421 can include a transmission 425 between a motor and the chuck 351 to effect a gear reduction to provide reduced rotational speed and increased torque for the chuck 351. The surgical system 100 can include a torque sensor associated with the rotary driver 421, and be operable to limit the torque applied to the effector and/or fastener 8 to reduce the risk of unwanted breakage. The rotary driver 421 is provided with a suitable source of energy, for example, a compressed fluid or electrical energy. In the illustrated structure, the driver 421 is an electric motor and is provided with electricity through an electrical conductor 426 that is operable to receive electricity through a connector 427 that is coupled to the robot 2, which has means for conducting electricity from a source (not shown) to the connector 427.

The tool 4 is provided with a chuck operator 431 that is operable on command to accomplish mounting of an effector 7 to the tool 4, and demounting of an effector 7 from the tool 4. As shown, a housing 435 is secured to the arm 414. The motor 421, transmission 425 and chuck 351 are all mounted in the housing 421. As shown, the housing 421 is generally cylindrical along at least a majority of its length and contains the motor 421 and transmission 425 in the interior of the housing 421. The chuck operator 431 is preferably powered and controlled remotely by components of the system 100, either by programming of the computer 230 and/or medical personnel.

Means is provided to effect powered remote operation of the chuck 351 for gripping and releasing the effector 7. The chuck 351 includes a hood 441 that is sleeved onto the housing 435 and movable longitudinally relative thereto. The hood 441 selectively engages the ball detent arrangement 418 to effect selective gripping of an effector shank 311. It is to be understood that the shank 311 could be provided with longitudinal flats to prevent relative rotation between the shank 311 and the chuck 351. As shown, the chuck operator 431 includes a link 443 that is secured to the hood 441 and couples the hood to an operator engine 447, such as a linear actuator. In the illustrated structure, the engine 447 includes a linear reciprocating device 449, such as a reciprocating fluid powered piston or an electric solenoid. In the illustrated structure, the device 449 is a fluid powered piston in a cylinder that is connected to a source of compressed fluid through the conduit 411 as described above. Upon command, the engine 447 will have a component reciprocate to effect movement of the hood 441 to either open the chuck 351 for receipt of a shank 311 therein or the release of a shank 311 therefrom.

All patents and publications mentioned in this specification are indicative of the levels of those skilled in the art to which the invention pertains.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

What is claimed is:

1. A surgical robot system comprising:
a multi axis surgical robot;
a tool adapted to be operably mounted on the robot, said tool being configured to releasably hold one of a plurality of surgical effectors in an effector attachment device on a distal end of said tool;
a computer coupled to the robot and operable to control operation of the robot and the tool; and
a magazine positioned adjacent the robot and having at least one first cradle adapted to releasably hold the plurality of surgical effectors in position for releasable attachment to and detachment from said tool with said effector attachment device when said tool is mounted on the robot and is positioned adjacent the cradle, said attachment and detachment of the surgical effector and movement of the robot being performed automatically on command and being under control of said computer, wherein one the plurality of surgical effectors is a driver configured to couple to a bone fastener allowing for installation of the bone fastener by the surgical robot, and wherein the tool includes a coupling component configured to engage the robot and having a central axis, the coupling component including a plurality of outwardly and circumferentially arranged projecting arms projecting radially outwardly to the central axis, each sized and shaped to be received in a respective one of a plurality of notches in the at least one cradle.

2. The surgical robot system of claim 1 wherein said effector attachment device including a chuck.

3. The surgical robot system of claim 1 including a tool changer mounted to the robot and operable to releasably mount said tool to said robot.

4. The surgical system of claim 3 including a second cradle adapted to hold a plurality of said tools for releasable attachment to said tool changer.

5. The surgical system of claim 4 wherein said first cradle having a plurality of spaced apart open-end slots and said second cradle having a plurality of spaced apart open-end spaces.

6. The surgical system of claim 4 wherein said first and second cradles being mounted on a platform positioned adjacent said robot.

7. The surgical system of claim 4 wherein at least one said effector including a driver and an associated fastener with said driver being adapted to be releasably retained by said tool.

8. The surgical robot system of claim 1, wherein the driver comprises an external thread and the bone fastener comprises an internal thread, the driver capable of threadingly engaging with the bone fastener.

9. The surgical robot system of claim 8, wherein the handedness of the driver threads and the bone fastener threads are the same.

10. A method of conducting surgery robotically comprising:

activating a multi axis surgical robot;

mounting a tool on the robot, said tool being configured to releasably hold any one of a plurality of surgical effectors in an effector attachment device on a distal end of said tool;

activating a computer coupled to the robot, controlling operation of the robot with the computer;

providing a magazine adjacent the robot, said magazine having at least one first cradle adapted to releasably hold the plurality of surgical effectors in position for releasable attachment to and detachment from said tool with said effector attachment device when said tool is mounted on the robot and is positioned adjacent the cradle, and automatically controlling on command said attachment and detachment of the surgical effector and movement of the robot with said computer, wherein one the plurality of surgical effectors is a driver configured to couple to a bone fastener allowing for installation of the bone fastener by the surgical robot, and wherein the tool includes a coupling component configured to engage the robot and having a central axis, the coupling component including a plurality of outwardly and circumferentially arranged projecting arms projecting radially outwardly to the central axis, each sized and shaped to be received in a respective one of a plurality of notches in the at least one cradle.

11. The surgical method of claim 10 wherein said effector attachment device including a chuck that attaches an effector to and releases an effector from said tool under control of the computer.

12. The surgical method of claim 10 including a tool changer mounted to the robot and controlling operation of the tool changer with said computer to releasably mount said tool to said robot.

13. The surgical method of claim 10, wherein the driver comprises an external thread and the bone fastener comprises an internal thread, the driver capable of threadingly engaging with the bone fastener.

14. The surgical method of claim 13, wherein the handedness of the driver threads and the bone fastener threads are the same.

* * * * *